(12) United States Patent
Silber et al.

(10) Patent No.: US 6,654,628 B1
(45) Date of Patent: Nov. 25, 2003

(54) METHODS TO ASSESS VASCULAR ENDOTHELIAL FUNCTION

(75) Inventors: Harry A. Silber, Owings Mills, MD (US); Jaoa A. C. Lima, Timonium, MD (US); David A. Bluemke, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/706,359

(22) Filed: Nov. 3, 2000

(51) Int. Cl.$^7$ .............................................. A61B 5/055
(52) U.S. Cl. ...................................... 600/410; 600/419
(58) Field of Search ................................ 600/410, 411, 600/419, 481, 485, 490

(56) References Cited

U.S. PATENT DOCUMENTS

| | | |
|---|---|---|
| 5,031,624 A | 7/1991 | Mistretta et al. |
| 5,277,182 A | 1/1994 | Koizumi et al. |
| 5,400,787 A | 3/1995 | Marandos |
| 5,517,992 A | 5/1996 | Opsahl et al. |
| 5,853,005 A * | 12/1998 | Scanlon ...................... 600/437 |

FOREIGN PATENT DOCUMENTS

WO   WO 95/12822   5/1995

OTHER PUBLICATIONS

Harry A. Silber, et al., "Arterial Flow–Mediated Dilatation is Linearly Proportional to Vascular Wall Shear Stress: Endothelial Function Assessed by Phase–Contrast Magnetic Resonance Angiography," Journal of the American College of Cardiology, vol. 35, No. 2, Suppl. A, Feb. 2000, p. 553A, XP 008001429, USA.

Copy of PCT International Search Report dated Mar. 27, 2002.

* cited by examiner

Primary Examiner—Ruth S. Smith
(74) Attorney, Agent, or Firm—Peter F. Corless; Lisa S. Hazzard; Edwards & Angell, LLP

(57) ABSTRACT

Featured are improved methods for non-invasive assessment of vascular endothelial function. The methods of the invention use phase contrast magnetic resonance imaging angiography to determine wall shear stress before, during, and after an arterial occlusion as well as the resulting endothelial dependent flow mediated dilation. Additionally methods are disclosed which allow for comparison of measurements derived through use of phase contrast magnetic resonance imaging to relate endothelial stimulus and response. The disclosed methods of the invention allow for reproducible, non-invasive diagnosis of early stage indicators of atherosclerosis.

15 Claims, 6 Drawing Sheets

METHODS TO ASSESS VASCULAR ENDOTHELIAL FUNCTION

STATEMENT REGARDING FEDERALLY-SPONSORED RESEARCH

The U.S. Government has a fully paid up, non-exclusive, nontransferable license to practice or have practiced for or on behalf of the United States this invention throughout the world as provided for by the terms of contract No. NO1HC951168 awarded by NIH (government agency).

FIELD OF INVENTION

The present invention relates to the field of non-invasive assessment of vascular endothelial function and more particularly to methods using phase contrast magnetic imaging angiography to determine flow mediated dilation and wall shear stress rates in order to determine vascular endothelial function in a patient.

BACKGROUND OF THE INVENTION

Vascular endothelial dysfunction has been found to be the earliest detectable occurrence in the development of atherosclerosis. Function of the vascular endothelium is affected by various factors including the presence of various substances such as oxidized low-density lipoprotein and nitric oxide, or by physical stimuli. Therefore, assessment of vascular physiology is important in detecting and tracking the development of early stage atherosclerosis. Additionally, it will also be crucial to studies in inflammation, stroke, hypertension and diabetes research, as well as additional complications affected by atherosclerosis.

Arterial smooth muscle relaxation is mediated by endothelial dependent mechanisms (Furchgott R F, Zawadski J V. The obligatory role of endothelial cells in the relaxation of arterial smooth muscle by acetylcholine. *Nature*. 1980;288:373.), which involve the release of nitric oxide (Palmer R, et al. Nitric oxide release accounts for the biologic activity of endothelium-derived relaxing factor. *Nature*. 1987;327:524–526.). In vitro, the primary hemodynamic determinant of endothelial release of nitric oxide and subsequent vasodilation is wall shear stress (WSS) (Koller A, Kaley G. Endothelial regulation of wall shear stress and blood flow in skeletal muscle microcirculation. *Am J Physiol*. 1991;260:H862–H868.; Koller A, et al. Role of shear stress and endothelial prostaglandins in flow- and viscosity-induced dilation of arterioles in vitro. *Circ Res* 1993;72:1276–1284.; Busse R, et al. Signal transduction in endothelium-dependent vasodilation. *Eur Heart J*. 1993; 14:Suppl I,2–9.; Busse R, Fleming I. Pulsatile stretch and shear stress: physical stimuli determining the production of endothelium-derived relaxing factors. *Journal of Vascular Research*. 1998;35:73–84.) Larger increases in non-pulsatile shear stress have been shown to produce greater increases in diameter of isolated arteries from rat skeletal muscle (Koller A, Kaley G. Endothelial regulation of wall shear stress and blood flow in skeletal muscle microcirculation. *Am J Physiol*. 1991;260:H862–H868.). However, the effects of pulsatile shear stress are different than those of constant shear stress (Ziegler T, et al. Influence of oscillatory and unidirectional flow environments on the expression of endothelin and nitric oxide synthase in cultured endothelial cells. *Arterioscler Thromb Vasc Biol*. 1998;18:686–692.; Malek A M, et al. Modulation by pathophysiological stimuli of the shear stress-induced up-regulation of endothelial nitric oxide expression in endothelial cells. *Neurosurgery*. 1999;45:334–344.).

In humans, reduced FMD, (flow-mediated dilation) in hypertension has been found to result from at least in part lower baseline systolic WSS (Khder Y, et al. Shear stress abnormalities contribute to endothelial dysfunction in hypertension but not in *type II diabetes*. *J. Hypertens*. 1998;16:1619–1625.). Conversely, an increase in blood flow following a brief period of skeletal muscle ischemia is accompanied by dilation of the conduit artery (Sinoway Li et al. Characteristics of flow-mediated brachial artery vasodilation in human subjects. *Cir Res*. 1989;64:32–42.; Celermajer D S, et al. Noninvasive detection of endothelial dysfunction in children and adults at risk of atherosclerosis. *Lancet*. 1992;340:1111.). Furthermore, increases in the magnitude or duration of hyperemia lead to increased vasodilation, while arterial diameter decreases during a low-flow state caused by distal arterial occlusion (Corretti M C, et al. Technical aspects of evaluating brachial artery vasodilation using high-frequency ultrasound. *Am J Physiol*. 1995;268:H1397–H1404.; Leeson P, et al. Non-invasive measurement of endothelial function: effect on brachial artery dilation of graded endothelial dependent and independent stimuli. *Heart*. 1997;78:22–27.). The relationship between WSS and arterial flow-mediated dilation (FMD) however, has not been established in humans.

Vascular physiology can be assessed, in part, through measurements of endothelial function. Changes in the diameter of an artery in response to a stimulus such as change in blood flow velocity through the artery (arterial wall shear stress, WSS) are indicative of endothelial function, known as flow mediated dilation (FMD). Endothelial function can be measured by inflating a blood pressure cuff around a subject's arm and monitoring velocity of blood flowing through a brachial artery while measuring the artery's diameter before, during and after the inflation of the cuff.

Ultrasound measurements of flow mediated dilation have been widely used to study endothelial function in patients with known cardiac risk factors with (Hoeks A P G, et al. Noninvasive determination of shear-rate distribution across the arterial lumen. *Hypertension*. 1995;26:26–33.; Levine G N, et al. Ascorbic acid reverses endothelial vasomotor dysfunction in patients with coronary artery disease. *Circulation*. 1996;93:210–214.; Vogel R A, et al. Changes in flow-mediated brachial artery vasoreactivity with lowering of desirable cholesterol levels in healthy middle-aged men. *Am J Cardiol*. 1996;77:37–40.; Motoyama T, et al. Endothelium-dependent vasodilation in the brachial artery is impaired in smokers: effect of vitamin C. *Am J Physiol*. 1997;273:H1644–H1650.; Plotnick G D, et al. Effect of antioxidant vitamins on the transient impairment of endothelial-dependent brachial artery vasoactivity following a single high-fat meal. *JAMA*. 1997;278:1682–1686.; Hornig B, et al. Vitamin C improves endothelial function of conduit arteries in patients with chronic heart failure. *Circulation*. 1998;97:363–368.; Neunteufl T, et al. Additional benefit of vitamin E supplementation to simvastatin therapy on vasoreactivity of the brachial artery of hypercholesterolemic men. *J Am Coll Cardiol*. 1998;32:711–716.; Chambers J C, et al. Demonstration of rapid onset vascular endothelial dysfunction after hyperhomocysteinemia: an effect reversible with vitamin C therapy. *Circulation*. 1999;99:1156–1160.) and without (Celermajer D S, et al. Noninvasive detection of endothelial dysfunction in children and adults at risk of atherosclerosis. *Lancet*. 1992;340:1111.; Celermajer D S, et al. Cigarette smoking is associated with dose-related and potentially reversible impairment of endothelium-dependent dilation in healthy young adults. *Circulation*. 1993;88:2149–2155.; Celermajer D S, et al.

Passive smoking and impaired endothelium-dependent arterial dilation in healthy young adults. *N Engl J Med.* 1996;334:150–154.) intervention. However, there is considerable overlap in the arterial dilatory response between individuals with and without cardiac risk factors (Corretti M C, et al. Technical aspects of evaluating brachial artery vasodilation using high-frequency ultrasound. *Am J Physiol.* 1995;268:H 1397–H1404.; Celermajer D S, et al. Cigarette smoking is associated with dose-related and potentially reversible impairment of endothelium-dependent dilation in healthy young adults. *Circulation.* 1993;88:2149–2155.; Celermajer D S, et al. Passive smoking and impaired endothelium-dependent arterial dilation in healthy young adults. *N Engl J Med.* 1996;334:150–154.). This is in part because FMD is inversely related to baseline diameter (Celermajer D S, et al. Noninvasive detection of endothelial dysfunction in children and adults at risk of atherosclerosis. *Lancet.* 1992;340:1111.). There is evidence from the study of rat skeletal muscle arterioles that this inverse relationship may be due to an inverse relationship between baseline diameter and wall shear stress (Koller A, Kaley G. Endothelial regulation of wall shear stress and blood flow in skeletal muscle microcirculation. *Am J Physiol.* 1991;260:H862–H868.).

Current methods to assess endothelial function non-invasively use ultrasound to measure flow mediated dilation of a limb artery after release of a temporary occlusion of that limb. However, use of ultrasound poses problems for assessment of vascular endothelial function. In addition to those technical problems discussed above wherein there is significant overlap of readings between patient populations, ultrasound measurements may be poorly reproducible because the technique is highly operator dependent with regard to probe positioning. Additionally, although dilation may be measured additional measurements to determine shear stress stimulus by ultrasound can only be accomplished using sophisticated, non-standard, signal processing equipment.

It thus would be desirable to provide novel methods for the non-invasive assessment of vascular endothelial function which are more effective, and reliable than current ultrasound methods. It also would be desirable that the new methods would not be dependent on the testing administrator; would generate consistent results; and would be readily adaptable to use for regular diagnostic screening protocols.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention features improved methods for non-invasive assessment of vascular endothelial function. Preferred methods of the invention use phase contrast magnetic resonance imaging to obtain images of an artery which can then be used to determine measurements to assess vascular endothelial function.

One preferred method of assessing vascular endothelial function of a subject during hyperemic response comprises:
(a) using a magnetic resonance imaging scanner to obtain images;
(b) locating an artery using coronal scout images;
(c) positioning the subject, such that the artery is parallel to a magnet bore of the magnetic resonance imaging scanner and cross sectional images can be obtained;
(d) constricting the artery for a time period, whereby the artery is fully occluded;
(e) releasing the artery from occlusion;
(f) acquiring images of the artery prior to occlusion (at baseline), as well as during occlusion, and at time periods following release from occlusion;
(g) calculating indicators of vascular endothelial function: wall shear stress and flow mediated dilation of the artery, from data acquired from the obtained images;
(h) determining a relationship between wall shear stress and flow mediated dilation;
(i) determining if the relationship between wall shear stress and flow mediated dilation is in a range of normal individuals and
(j) determining if the relationship between wall shear stress and flow mediated dilation is outside the range of normal individuals, whereby a relationship outside the range is indicative of abnormal vascular endothelial function.

An additional preferred method of the invention include methods determining arterial wall shear stress during hyperemic response, wherein steps of obtaining images of an artery prior to, during, and following occlusion of the artery are identical to those of the abovementioned method, and further comprise steps of determining indicators of vascular endothelial function such as wall shear stress throughout the process of occlusion and resulting hyperemia, from calculations using data generated through obtained images.

An additional preferred aspect of the invention includes determination of a pattern of the time course of wall shear stress throughout the process of occlusion and resulting hyperemia and compare the pattern to one of normal individuals.

Another preferred method of the invention includes methods of determining a relationship between shear stress stimulus and dilation response during hyperemic response, wherein steps of obtaining images of an artery prior to, during, and following occlusion of the artery are identical to those of the abovementioned method, and further comprise steps of determining indicators of vascular endothelial function such as wall shear stress and flow mediated dilation from calculations using data generated from images, followed by determining a relationship between the obtained shear stress stimulus value or the change in wall shear stress as compared from baseline to peak hyperemia and the obtained dilation response value.

A further preferred method of the invention includes methods of determining a relationship between arterial diameter and hyperemic wall shear stress, wherein steps of obtaining images of an artery prior to, during, and following occlusion of the artery are identical to those of the abovementioned method; and further comprise steps of determining the artery diameter at baseline and the wall shear stress following release of occlusion from calculations using data generated from obtained images; and determining a relationship between the wall shear stress generated and the size of the artery.

Additionally provided are diagnostic methods of evaluating vascular endothelial functions of patients having cardiac risk factors, using the methods provided herein.

Other aspects and embodiments of the invention are discussed below.

DETAILED DESCRIPTION OF THE INVENTION

Figure 1:
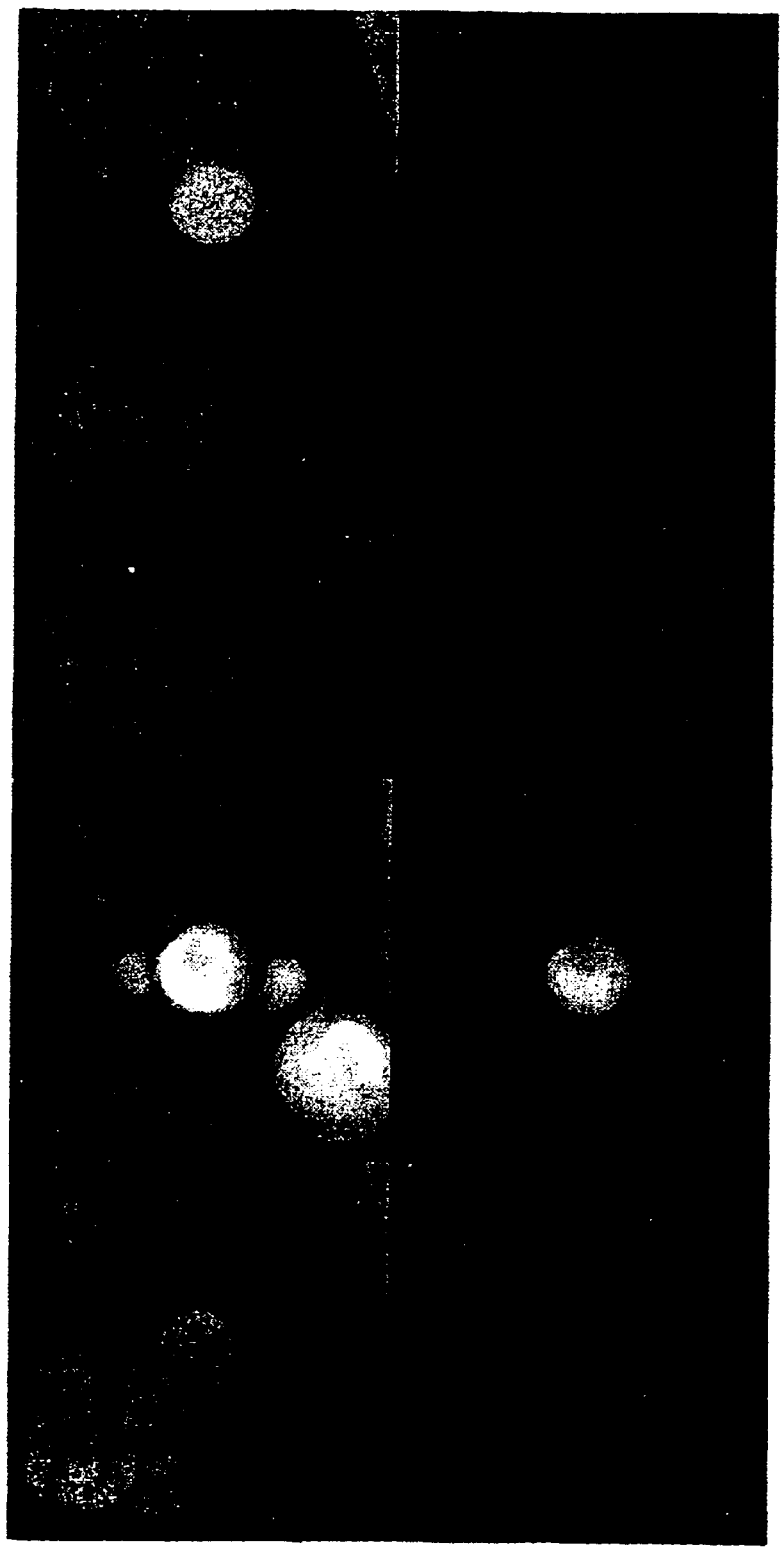
FIG. 1 depicts phase contrast images of a brachial artery in a patient.

We have developed a method to assess vascular endothelial function using phase contrast magnetic resonance angiography. More specifically, this method provides for determining the relationship between wall shear stress during peak post-ischemic hyperemia and resulting arterial dilation in humans. The provided methods allow comparison of wall shear stress stimulus to flow mediated responses when assessing vascular endothelial function.

Phase contrast magnetic resonance angiography (PCMRA) allows for images which can provide cross sectional area and spatially averaged blood flow velocity readings simultaneously; thus, it readily allows for the calculation of vascular wall hear stress (WSS) as well as simultaneous reading of degree of dilation or flow mediated dilation (FMD). A fixed cross section can be imaged repeatedly, thus reducing operator dependence. Quantification of the stimulus-response relation in FMD, as well as additional indicators of vascular endothelial function allow for improved methods of assessment of vascular endothelial function and determination and diagnosis of early stage factors affecting atherosclerosis.

As discussed above, provided are methods of assessing vascular endothelial function using phase contrast magnetic resonance angiography (PCMRA). In general, the method consists of the following:

- a person lies in scanner with a receiver coil and a sphygmomanometer, or inflatable (blood pressure)cuff on the limb;
- phase contrast magnetic resonance images are obtained of the arterial cross section at baseline;
- the cuff is inflated to a pressure above the maximum systolic pressure of the person in order to block the artery completely, for a period of about five minutes, then the pressure is released; and
- phase contrast magnetic resonance images are obtained of the arterial cross section at intervals following release of occlusion. From the obtained images, the diameter of the artery is determined and the changes in artery diameter, a measurement of flow mediated dilation (FMD), as well as the wall shear stimulus for FMD are determined.

Scanning images may be taken at any intervals from immediately post release of occlusion of the artery through any stage of recovery, including two, five, or ten minutes post release. Depending on when the scans and images are taken, the data generated will yield various relationships.

For example, PCMRA images are obtained of the arterial cross section at about 1 minute to about 5 minutes after cuff release, when flow mediated dilation has occurred. From these images the FMD response is determined.

Additionally, PCMRA images are obtained during peak reactive hyperemia, within about 20–30 seconds to about 1 minute after cuff release. From the data generated from these images, hyperemic wall shear stress is determined.

To calculate wall shear stress from the cross-sectional PCMRA image of an artery, the cross section is circumscribed. The average blood flow velocity across the cross section is calculated, as is cross sectional area. Wall shear stress as well as flow mediated dilation are calculated as detailed in methods and examples described herein.

FMD, calculated as the percent increase in diameter from baseline to about 1 minute after occlusion release, can be then compared to wall shear stress during peak reactive hyperemia, calculated as wall shear stress during systole during the about 20–30 second period after cuff release.

Use of PCMRA for measurement of vascular endothelial indicators provides a quantitative relation between peak WSS during peak hyperemia and FMD. Results assessing normal individuals suggest that measuring peak WSS during the hyperemia immediately following 5 minutes of arterial occlusion is a simple way of relating stimulus to response in endothelial dependent FMD (see methods, examples and figures contained herein).

Using PCMRA in the brachial artery of healthy individuals, the FMD response has been shown to be linearly proportional to the systolic WSS stimulus that occurs during peak hyperemia. Additionally, the reason why the FMD response is greater in small arteries than responses seen in large arteries appears to be because the hyperemic WSS stimulus is greater in small arteries, as indicated also in studies contained herein using PCMRA (see examples).

Each PCMRA scan took 15–25 seconds. Therefore peak systolic cross sectional area at about 1 minute after cuff release is an average value for peak systole in that scanning interval. However, the incremental change in diameter during a 15–25 second interval at 1 minute post cuff release is minimal (Corretti M C, et al. Technical aspects of evaluating brachial artery vasodilation using high-frequency ultrasound. *Am J Physiol.* 1995;268:H1397–H1404.). Additionally, a measure of hyperemic peak WSS over a finite interval of its occurrence may be more useful than one instantaneous measurement because stimulus to dilate requires some finite exposure to supra-normal flow (Leeson P, Thorne S, Donald A, Mullen M, Clarkson P, Deanfield J. Non-invasive measurement of endothelial function: effect on brachial artery dilation of graded endothelial dependent and independent stimuli. *Heart.* 1997;78:22–27.).

When compared to a related study where peak systolic WSR (wall shear rate) and peak systolic WSS were measured using a special micrometric ultrasound technique, results using PCMRA methods differ by only 5.4% (see Simon A C, et al. Pulsatile flow and oscillating wall shear stress in the brachial artery of normotensive and hypertensive subjects. *Cardiovascular Research* 1990; 24: 129–136). Thus, the present methods allow for effective screening of endothelial function in individuals using a standard modern MRI scanner.

There are differences in the way diameter is obtained using PCMRA from that of ultrasound. Using ultrasound, the diameter measurements cannot readily be timed to peak flow and are commonly made at the time of the R-wave, as with PCMRA. With PCMRA, scans are done at peak flow, because that is the time of peak signal contrast between the lumen and the vessel wall. Hence, the vessel diameter is slightly larger by PCMRA (p=0.009, see FIG. 4 and examples).

In the PCMRA protocol, the occluding cuff was placed on the upper arm to maximize sensitivity in measuring FMD.

This is because hyperemia and FMD are greater after upper arm occlusion than after lower arm occlusion (Vogel R A, et al. A comparison of brachial artery flow-mediated vasodilation using upper and lower arm arterial occlusion in subjects with and without coronary risk factors. *Clin Cardiol.* 2000;23:571–575.). The cuff was placed on the lower arm in the ultrasound protocol to maximize stability in imaging the brachial artery. Thus, FMD was greater using the PCMRA protocol (p<0.0001). Additionally, in the ultrasound protocol, the cuff was inflated to between 200–300 mmHg to assure occlusion, because images cannot be taken to determine full occlusion. In the PCMRA protocol, images can be taken through the occlusion cuff therefore the cuff was inflated only to 10–30 mmHg above systolic pressure. Therefore, no differences in percent change in diameter should result from this procedural difference, however, use of the PCMRA methods allow for reduced discomfort in patients undergoing testing.

Thus, when contrasting PCMRA with ultrasound techniques, the methods of the present invention allow for several important advantages over the previous methods. A fixed cross sectional image may be repeatedly imaged. This eliminates the need for an operator to ensure the probe is capturing the true diameter of the same arterial cross section during each acquisition. By reducing operator dependence, PCMRA will improve reproducibility.

Additionally, the sophistication of an MRI scanner allows for variable placement and use of the occlusion cuff, thereby allowing for the most sensitive readings, while causing less discomfort to the patient.

Figure 6:
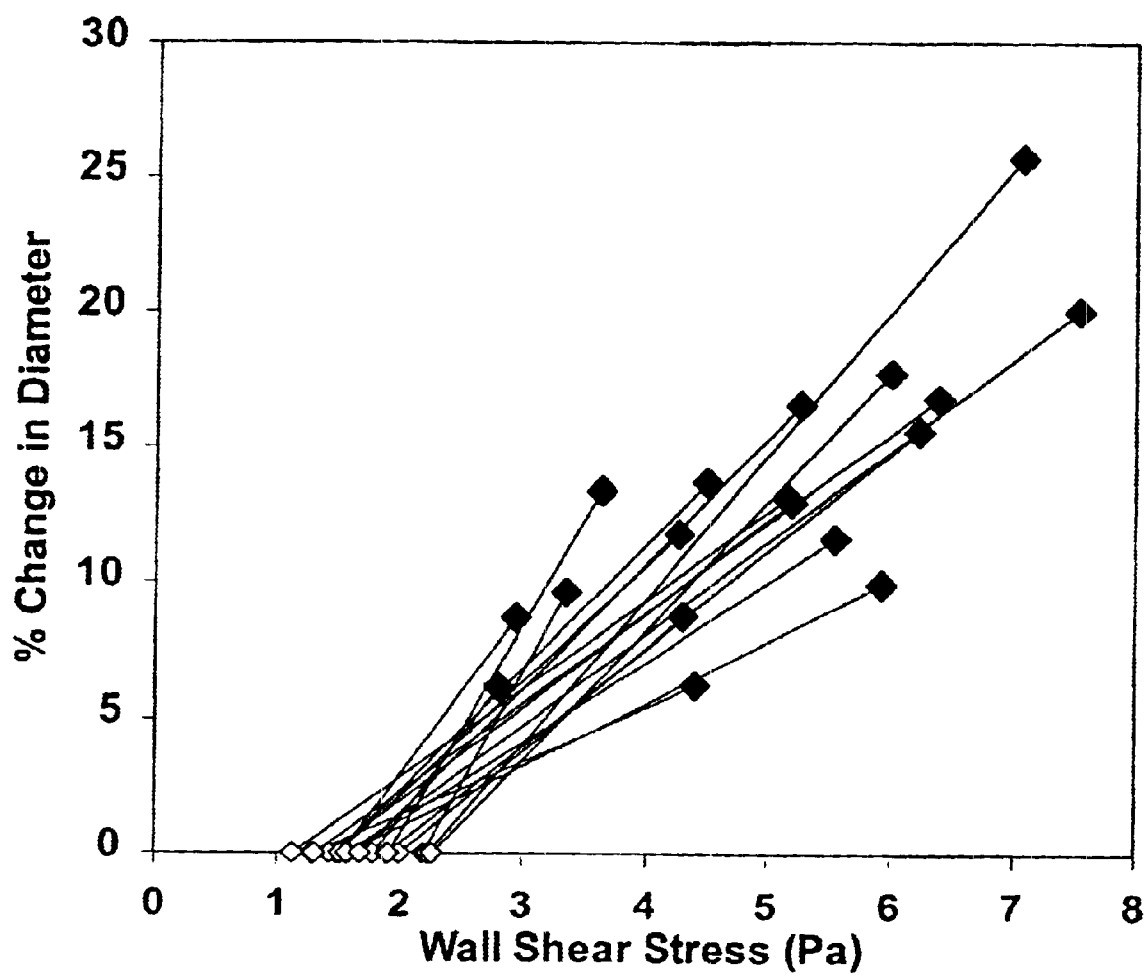
FIG. 6 depicts the range of wall shear stress from baseline to hyperemic conditions.

Finally, because PCMRA images cross sectional area and velocity flow simultaneously, it readily allows for calculation of wall shear stress, the stimulus for FMD. Since the magnitude of post ischemic hyperemia and thus hyperemic peak WSS varies among individuals (see examples and FIG. 6), the stimulus for FMD cannot be easily controlled. Therefore, comparing the magnitude of the stimulus to the magnitude of the response will enhance the ability to identify endothelial dysfunction in patients.

All documents mentioned herein are fully incorporated herein by reference in their entirety. The following non-limiting examples are illustrative of the invention.

METHODS

Unless otherwise noted, the following methods and materials were used in the ensuing examples of the invention.

Study Population.

18 healthy nonsmokers were studied, age range 25 to 46 years, without hypertension, diabetes, hyperlipidemia, obesity or cardiac disease in a first-degree relative. No volunteer was on cardiovascular medications. For the protocol comparing diameter measurements by ultrasound and PCMRA, 9 healthy volunteers were studied, age range 30 to 56 years, with no known coronary disease, however cardiac risk factors were not excluded. The subjects gave informed consent, all procedures were performed in accordance with institutional guidelines, and the study was approved by the institutional review board.

Study Protocol.

Peak systolic WSS and vessel dilation in response to hyperemia were measured in the right brachial artery of each subject. Each subject abstained from alcohol, caffeine, milk and food for at least 6 hours before the study. A sphygmomanometer cuff was placed on the upper arm. A 3 inch receiver coil was placed on the medial aspect of the arm, outside of the cuff. Electrocardiographic leads were placed on the thorax. The subject was placed supine, head-first, into a 1.5T MRI scanner (CV/i, General Electric Medical Systems, Milwaukee. Wis.) equipped with cardiac gradient coils (40 mT/m, 120 T/m/s). The subject's brachial artery was located using coronal scout images. The arm was positioned using coronal, sagittal and/or axial scout images to ensure that the brachial artery was parallel to the magnet bore. Baseline phase-contrast MR images were obtained. After baseline blood pressure was recorded, the cuff was inflated to at least 10 mmHg above peak systolic pressure for 5 minutes. Phase-contrast scans were acquired during cuff occlusion, during peak hyperemia immediately after cuff deflation, and at 1 minute after cuff deflation.

Phase Contrast Magnetic Resonance Angiography (PCMRA) Imaging Protocol.

A single imaging plane perpendicular to the brachial artery was prescribed. Each two-dimensional phase contrast scan yielded 20 magnitude images and 20 corresponding phase images, reconstructed from 20 equally spaced time points in the cardiac cycle. Scan duration was 15 to 25 sec. An ECG-gated sine phase-difference phase-contrast sequence was used. The imaging parameters were: TR 10.8 msec, TE 4.8 msec, field-of-view 8 cm×8 cm, matrix size 256×224 pixels (pixel size 0.48 mm×0.31 mm), slice thickness 8 mm, maximum encoded velocity 250 cm/sec along the superior/inferior axis, 16 views per segment, first order flow compensation with view-sharing, bandwidth 31.2 kHz, flip angle 25. The maximum encoded velocity value was chosen to accommodate the greatly increased velocity during peak hyperemia. The field-of-view and matrix size correspond to a pixel resolution of 8.96 pixels/mm$^2$. An arterial lumen with a circular cross section 3 mm in diameter would thus be represented by 63 pixels. A 4 mm diameter lumen would consist of 113 pixels, and a 5 mm diameter lumen would consist of 176 pixels. The imaging parameters were in accord with optimal criteria suggested for using MRI to measure blood vessel diameter (Hoogeveen R M, Bakker C J G, Viergever M A. Limits to the accuracy of vessel diameter measurement in *MR angiography. JMRI* 1998; 1228–1235.).

Data Analysis.

Using commercially available flow analysis software (General Electric), the artery lumen in each image was outlined with a region-of-interest tool. Cross-sectional area was obtained as the average of three measurements made at the cardiac phase where peak flow occurred. Spatially averaged blood flow velocity ($V_{SA}$) was calculated from the same specific phase. Because the region-of-interest tool approximated the lumen edge with a series of curved segments rather than a circle, the calculation of cross-sectional area and $V_{SA}$ did not require the assumptions about cross-section geometry, or the shape of the blood flow velocity profile. In calculating average vessel diameter (D) from cross-sectional area (A), a circular cross-section was assumed:

$$D=2(A/\pi)^{1/2}.$$

Peak systolic wall shear rate (WSR) was calculated as $$\text{Peak WSR}=2(n+2)(V_{SA})/D,$$

where n determines the bluntness of a paraboloid velocity distribution, (Hoeks A P G, Samijo S K, Brands P J, Reneman R S. Noninvasive determination of shear-rate distribution across the arterial lumen. *Hypertension*. 1995;26:26–33.). For a fully developed parabola, n equals 2. The velocity profile in the brachial artery during systole, is blunted (see Simon A C, Levenson J, Flaud P. Pulsatile flow and oscillating wall shear stress in the brachial artery of normotensive and hypertensive subjects. *Cardiovascular Research*. 1990; 24: 129–136.), thus n is greater than 2. To determine n, we calculated the ratio of the center systolic velocity ($V_C$) to the spatially averaged systolic velocity for the two baseline scans and for peak hyperemia in 15 subjects. For a paraboloid profile, $$V_{SA}=n(V_C)/(n+2).$$

$$n=2/((V_C/V_{SA})-1)$$

The average $V_C/V_{SA}$ of the 15 subjects was used to calculate n. Peak systolic wall shear stress (peak WSS) was calculated by multiplying peak WSR by blood viscosity. As blood is a non-Newtonian fluid, its viscosity varies at different shear rates. (See, Fung Y C. *Biomechanics: Circulation*, $2^{nd}$ ed. New York: Springer-Verlag, 1998.) After all the shear rates were calculated, a viscosity value was used which corresponded to the observed range of shear rates. (See, Brands P J, Hoeks A P G, Hofstra L, Reneman R S. A noninvasive method to estimate wall shear rate using ultrasound. Ultrasound in *Med Biol*. 1995;21:171–185.)

Several assumptions were made using our calculations. First, we assumed a circular cross-section in calculating diameter from arterial cross-sectional area, however not when measuring area itself. Thus, the calculated diameter is an average for a cross-section that is at least approximately circular. This is clearly more robust than choosing only one or two diameters to measure.

We assumed axial symmetry in the flow velocity profile when calculating WSS from spatially averaged velocity. However, we did not need to make this assumption when measuring velocity. In determining a value for blood viscosity, we did not measure hematocrit, but assumed it to be normal in these healthy individuals. Importantly, we did not assume that the artery was rigid, or that flow was constant. The formula we used applies to pulsatile flow in a distensible artery.

We assumed that the velocity profile during peak systole is a blunted paraboloid. This assumption is supported by studies on pulsatile flow in distensible tubes (Fung Y C. *Biomechanics: Circulation*, $2^{nd}$ ed. New York: Springer-Verlag, 1998.; Nichols W W, O'Rourke M F. McDonald's Blood Flow in Arteries: *Theoretical, Experimental and Clinical Principles*, $4^{th}$ ed. London: Arnold, 1998.) and by actual measurements in the brachial artery using special micrometric ultrasound (Simon A C, et al. Pulsatile flow and oscillating wall shear stress in the brachial artery of normotensive and hypertensive subjects. *Cardiovascular Research*. 1990; 24: 129–136.). Our data actually show the velocity profile to be slightly skewed; that is, the peak of the paraboloid is not at the exact center of the arterial cross-section. However, the average fractional distance from the location of the maximum flow velocity to the center of the arterial cross-section was only 0.27. With this fractional distance, the difference between assuming symmetry and skewness in calculating peak systolic WSS is only 2%.

Ultrasound Correlation Protocol.

Nine healthy subjects with no known coronary disease, age range 30 to 56 years, underwent the PCMRA protocol and a similar FMD protocol using a standard ultrasound approach (Celermajer D S, et al. Noninvasive detection of endothelial dysfunction in children and adults at risk of atherosclerosis. *Lancet*. 1992;340:1111.). The ultrasound FMD protocol was performed 3 times for each subject: 2 times, spaced 15 minutes apart in the first session, and a third time one week later. The ultrasound and PCMRA protocols were carried out at the same time of the day, and within 3 months of each other for each subject. Subjects abstained from food, coffee, alcohol, and cigarettes for at least 6 hours before the ultrasound test, as with the PCMRA protocol. ECG leads were placed on the chest. The skin was marked at a satisfactory probe position approximately 5 cm proximal to the antecubital fossa. An inflatable cuff was placed on the right forearm. A 7.0 MHz ultrasound transducer (Hewlett Packard, Palo Alto, Calif.) was used to image the right brachial artery. After baseline measurements the cuff was inflated to 200 mmHg for 5 minutes, then deflated. The brachial artery was scanned continuously and images were recorded at 1 minute after cuff deflation. The images were recorded on disk. Analyses were performed off-line. As with PCMRA, FMD was calculated as the percent change in diameter from baseline to 1 minute post-cuff release. The 3 ultrasound measurements were averaged for each subject.

Statistical Analysis.

Results are expressed as mean value ± standard deviation. Linear regression analysis was used to 1) assess the relation between percent change in diameter and hyperemic peak systolic WSS or change in peak systolic WSS, 2) assess the relation between baseline diameter and each of the following: hyperemic systolic $V_{SA}$, hyperemic systolic diameter, hyperemic peak systolic WSS, and percent change in diameter, 3) compare diameter, change in diameter, and percent change in diameter between ultrasound and PCMRA. A p-value less than 0.05 was considered significant.

Intra-observer and inter-observer reliability was calculated for the PCMRA technique according to Fleiss (see, Fleiss J L. *The Design and Analysis of Clinical Experiments*. New York: John Wiley and Sons, 1986, 1–21.) as follows:

Intra-observer reliability of PCMRA was calculated for diameter and peak WSS by two methods, 1) Intra-observer reliability coefficient Cronbach's alpha, and 2) coefficient of variation=(SD/mean)*100.

To calculate inter-observer reliability of the PCMRA technique, images from 8 of the subjects were analyzed by two observers who were blinded to the subjects' identities and to each other's measurements. Each observer independently measured cross-sectional area 3 times. Inter-observer reliability coefficient was calculated for arterial diameter and peak WSS.

EXAMPLE 1

Relationship Between Shear Stimulus and Dilation Response.

Magnitude and phase images of the brachial artery during peak flow were taken of subjects during maximum hyperemia, at baseline, immediately after cuff release, and 1 minute after cuff release, using PCMRA. Exemplary images are shown in FIG. 1 (M=magnitude images, P=phase images) for a typical subject. Increased blood flow velocity is linearly encoded as higher intensity in the phase images. After baseline images (A) are obtained, the artery is occluded (B), during which there is no flow. Immediately after release of arterial occlusion (C), the intensity is greatly increased, reflecting the hyperemia. One minute after cuff release (D), the artery size has increased compared with baseline. Areas of increased blood flow also have a higher intensity in the magnitude images due to non-linear flow effects.

Spatially averaged flow velocity and center systolic velocity were determined from calculations using data generated via the PCRMA protocol. The average Vc/Vsa for the subset of 15 subjects was 1.69 at baseline and did not change during peak hyperemia (p=0.87). Thus, n=2.9 for both baseline and peak hyperemia. Therefore, n=3 was used to calculate peak WSR.

Peak WSR at baseline and immediately after occlusion release, and diameter at baseline and 1 minute after occlusion release were calculated. Results are shown in Table 1. For the range of shear rates encountered in this study, blood viscosity varies between 0.0032 and 0.0034 Pa-s (Brands P J, Hoeks A P G, Hofstra L, Reneman R S. A noninvasive method to estimate wall shear rate using ultrasound. *Ultrasound in Med Biol.* 1995;21:171–185.). Therefore, we used viscosity=0.0033 Pa-s to calculate peak WSS. Peak WSS increased from 1.68±0.34 Pa at baseline to 5.03±1.37 Pa immediately after cuff release (p<0.0001, see Table 1). Vessel diameter increased from 3.84+0.60 mm at baseline to 4.34+0.58 mm one minute post-cuff release (p<0.0001, see Table 1).

Figure 2:
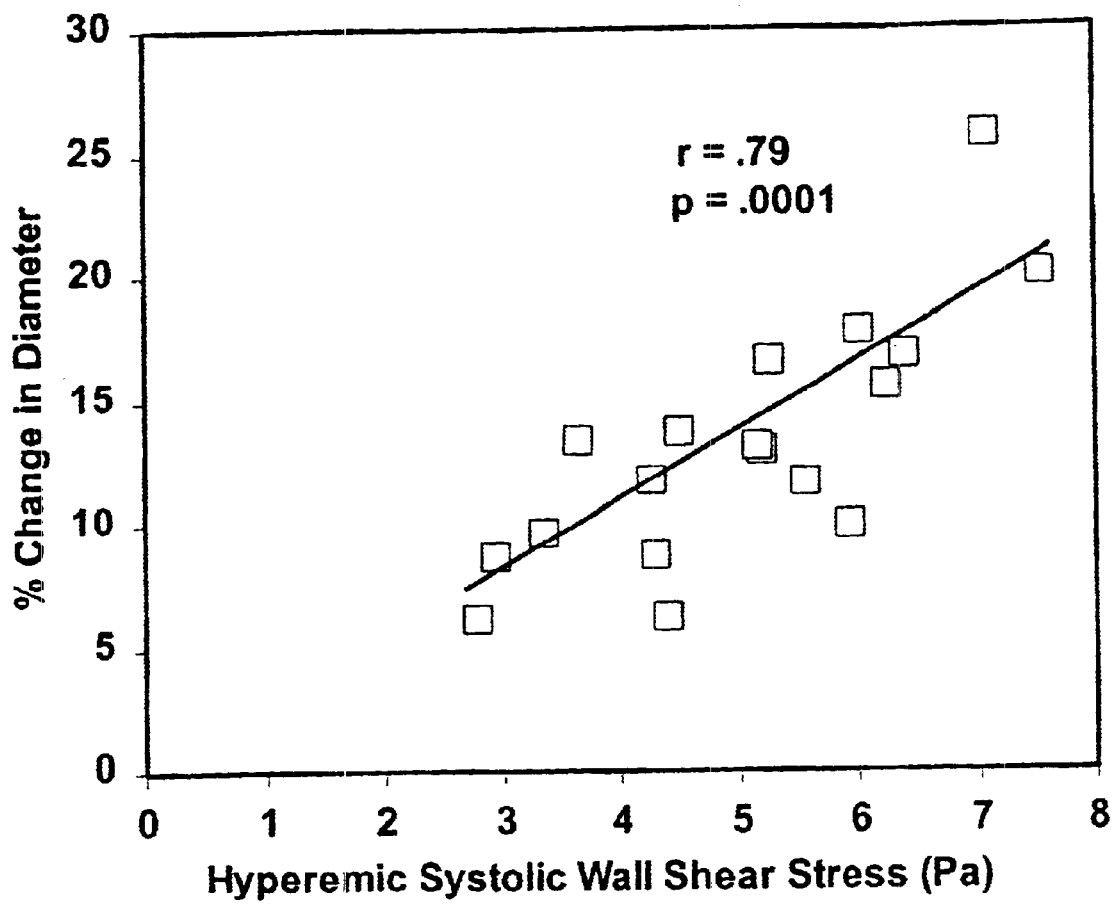
FIG. 2 depicts the relationship between flow mediated dilation and systolic wall shear stress during peak hyperemia.

From these results, the relationship between shear stress and dilation response was determined. The relationship between peak systolic WSS during peak hyperemia and percent change in diameter from baseline to one minute post cuff release is depicted in FIG. 2. Percent change in diameter is linearly proportional to peak systolic WSS during hyperemia with a high correlation (r=0.79, p=0.0001).

Figure 3:
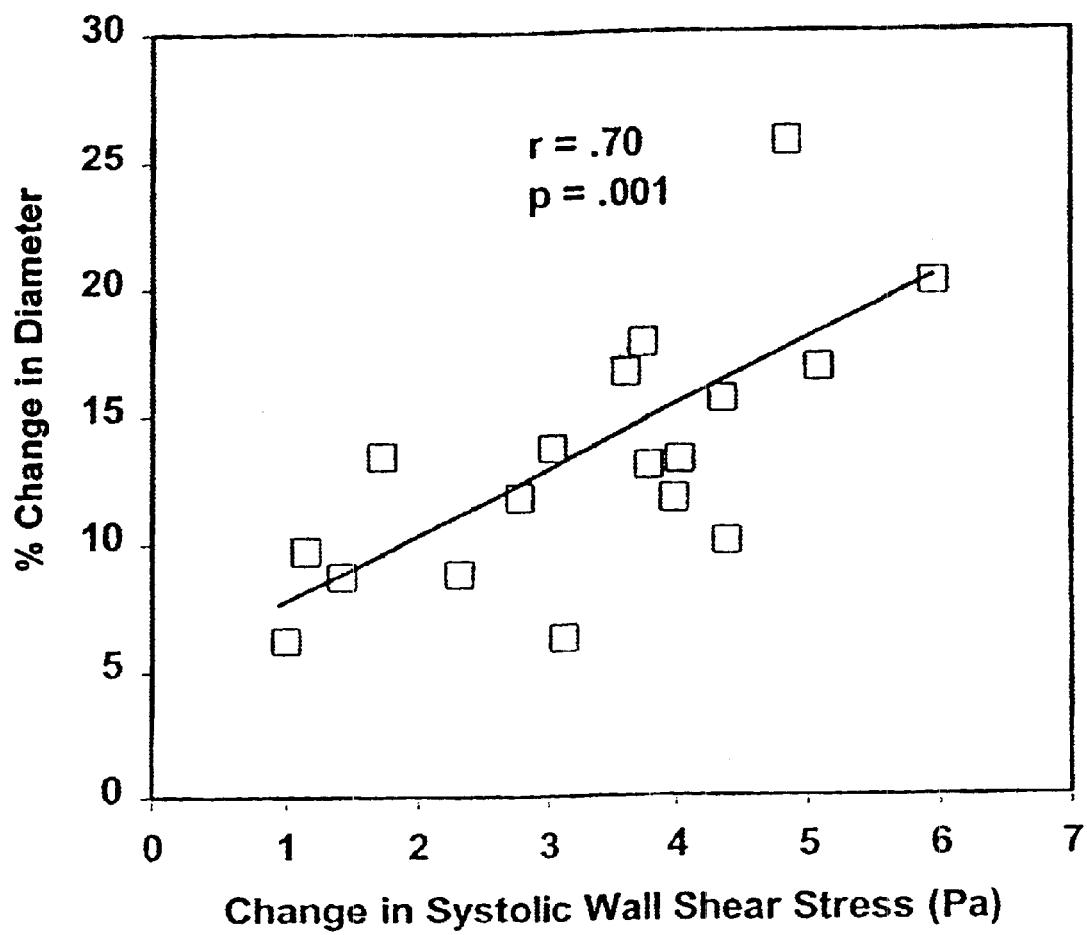
FIG. 3 depicts the relationship between flow mediated dilation and the change in systolic wall shear stress from baseline to peak hyperemia.

We also compared the dilation response to the change in shear stress. Percent change in diameter is also linearly proportional to the change in peak systolic WSS from baseline to hyperemia (r=0.70, p=0.001, see FIG. 3).

Reliability: The intra-observer coefficient of variation was 1.0% for diameter and 3.2% for peak WSS. Intra-observer reliability (Cronbach's alpha) was greater than 0.99 for diameter and was 0.99 for peak WSS. Inter-observer reliability was 0.98 for diameter and 0.92 for peak WSS.

TABLE 1

Subject Characteristics and Measurements

| | | | Diameter | | | Sys. WSR ($s^{-1}$) | | Sys. WSS (Pa) |
|---|---|---|---|---|---|---|---|---|
| Subject | Age | M/F | Base | 1 min | (%) | Base | Peak | Peak |
| 1 | 26 | F | 3.42 | 3.89 | 13.7 | 449 | 1367 | 1.48 4.51 |
| 2 | 39 | F | 4.02 | 4.41 | 9.7 | 663 | 1014 | 2.19 3.35 |
| 3 | 30 | F | 3.49 | 4.19 | 20.1 | 482 | 2286 | 1.59 7.54 |
| 4 | 31 | M | 5.09 | 5.54 | 8.8 | 606 | 1305 | 2.00 4.31 |
| 5 | 38 | M | 5.02 | 5.61 | 11.8 | 451 | 1294 | 1.49 4.27 |
| 6 | 32 | M | 4.20 | 4.46 | 6.2 | 541 | 845 | 1.79 2.79 |
| 7 | 31 | M | 4.39 | 4.96 | 13.0 | 429 | 1576 | 1.42 5.20 |
| 8 | 45 | F | 3.93 | 4.27 | 8.7 | 457 | 890 | 1.51 2.94 |
| 9 | 41 | F | 3.69 | 4.12 | 11.7 | 479 | 1686 | 1.58 5.56 |
| 10 | 39 | M | 4.31 | 4.58 | 6.3 | 388 | 1336 | 1.28 4.41 |
| 11 | 36 | M | 3.78 | 4.28 | 13.2 | 343 | 1563 | 1.13 5.16 |
| 12 | 37 | F | 3.03 | 3.81 | 25.7 | 675 | 2145 | 2.23 7.08 |
| 13 | 35 | F | 3.46 | 4.04 | 16.8 | 394 | 1936 | 1.30 6.39 |
| 14 | 29 | F | 3.79 | 4.17 | 10.0 | 474 | 1801 | 1.56 5.94 |
| 15 | 25 | F | 3.01 | 3.48 | 15.6 | 570 | 1891 | 1.88 6.24 |
| 16 | 30 | F | 3.20 | 3.73 | 16.6 | 506 | 1598 | 1.67 5.27 |
| 17 | 23 | F | 3.35 | 3.80 | 13.4 | 579 | 1102 | 1.91 3.64 |
| 18 | 28 | M | 4.00 | 4.71 | 17.8 | 687 | 1821 | 2.27 6.01 |
| Mean | 33 | | 3.84 | | 13.3 | 510 | 1525 | 1.68 5.03* |
| (St Dev) | (6) | | | 4.34* | (5.0) | (102) | * | (.34) (1.37) |

Base indicates baseline value; Diameter 1 min, diameter at 1 minute after cuff release; Sys. WSR, systolic wall shear rate; Sys. WSS, systolic wall shear stress; Peak, peak hyperemia immediately after cuff release; * indicates change from baseline (p<0.0001)

EXAMPLE 2.

PCMRA Compared With Ultrasound.

Figure 4:
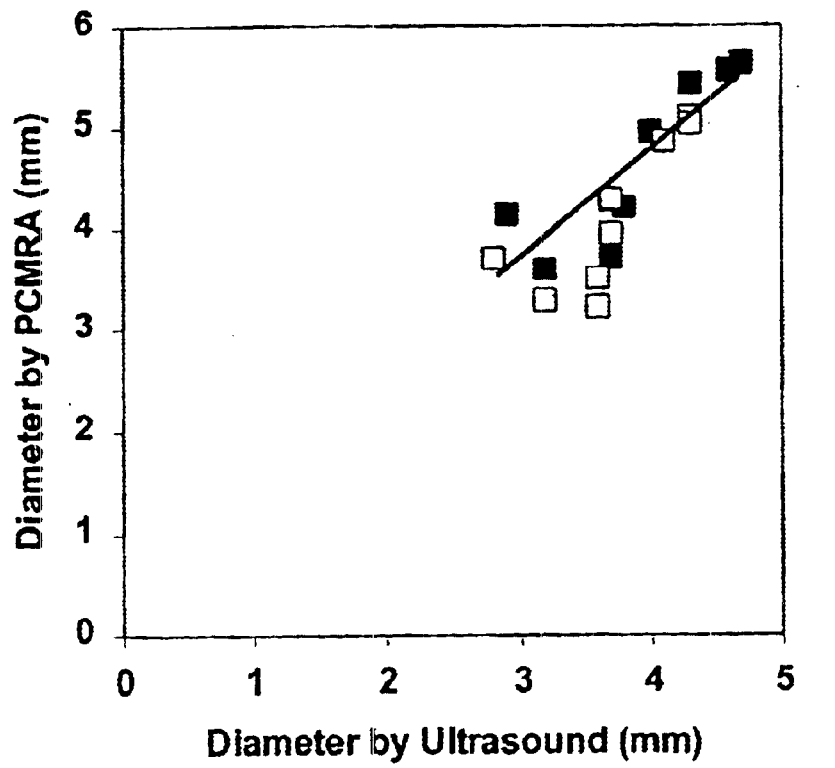
FIG. 4 depicts the relationship between diameter measurements as obtained using PCMRA and ultrasound methods.
Figure 4:
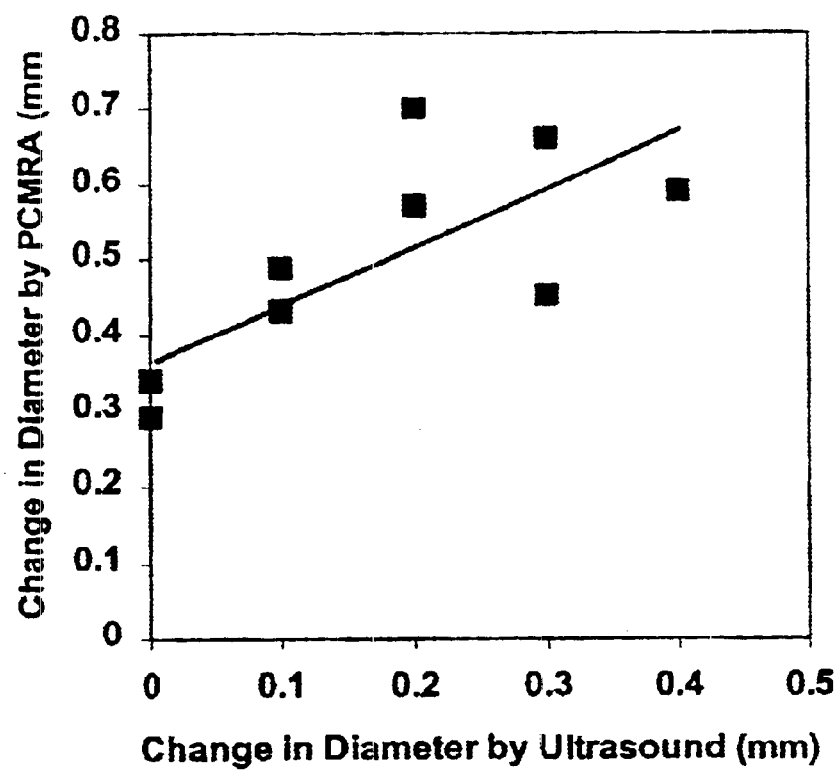

Brachial artery images during peak flow were taken of nine subjects during maximum hyperemia, at baseline, immediately after cuff release, and 1 minute after cuff release, using PCMRA as well as with a similar ultrasound protocol, and results were compared (see Table 2, FIG. 4). Brachial artery diameter measurements between ultrasound and PCMRA were highly correlated at baseline (r=0.84, p<0.01, Table 2, FIG. 4). However, diameter was greater by PCMRA than by ultrasound 4.1+0.7 mm vs. 3.7+0.5 mm, p=0.009). The correlation between absolute diameter change by ultrasound and PCMRA was statistically significant (r=0.72, p=0.03). However, the correlation between the percent change in diameter by ultrasound and PCMRA was not statistically significant (p=0.55). This is probably due to dividing the change in diameter (greater by PCMRA) by baseline diameter (also greater by PCMRA).

EXAMPLE 3.

Relationship Between Flow Mediated Dilation and Baseline Diameter

Figure 5:
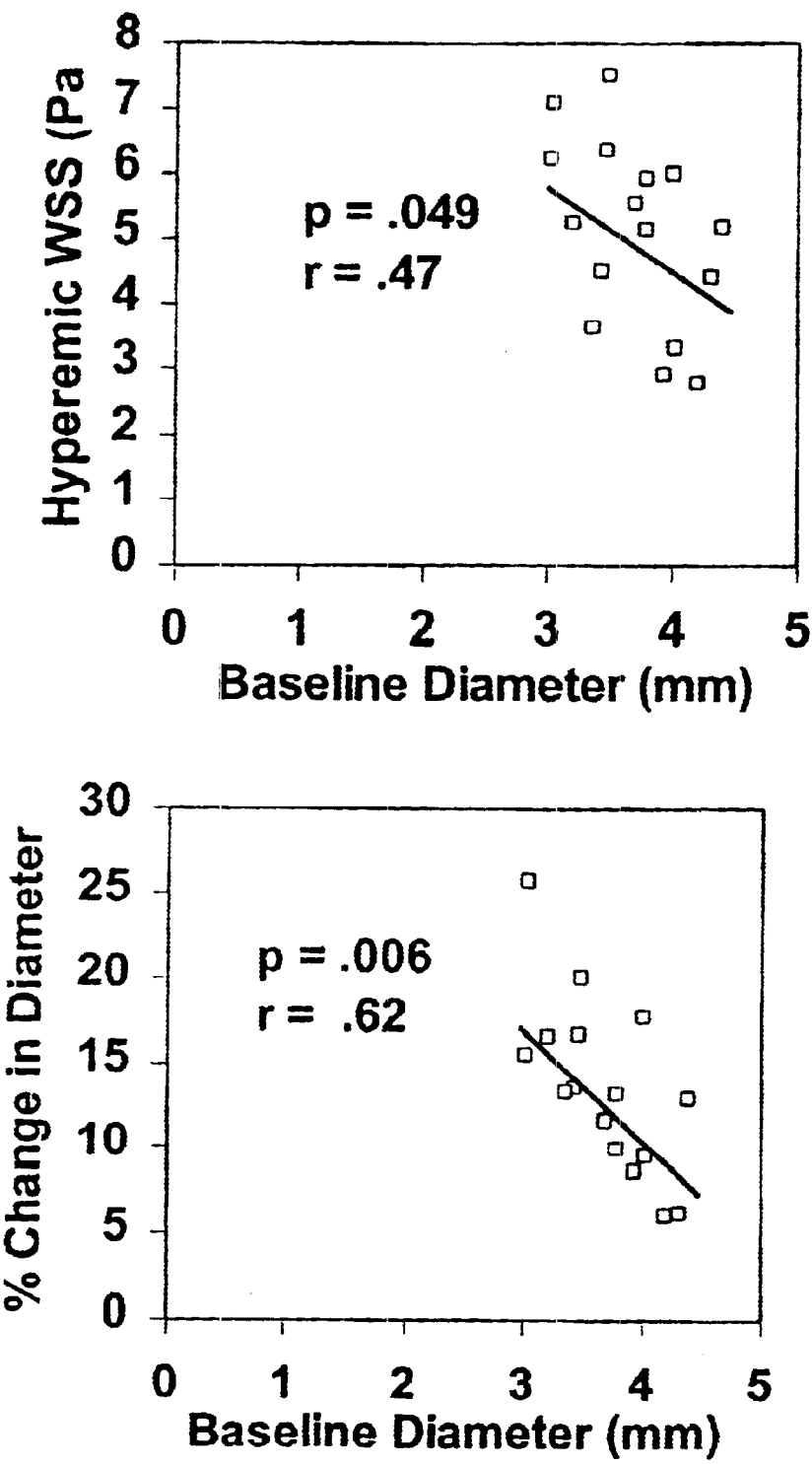
FIG. 5 depicts the relationship between shear stress stimulus and baseline arterial size and the relationship between endothelial flow mediated dilation response and baseline arterial size.

In order to look at the relationship of shear stress and dilation response in the context of vessel size, magnitude and phase images of the brachial artery were taken of subjects using PCMRA, and measurements calculated as discussed in the methods and in Example 1. WSS is considered to be the primary hemodynamic stimulus in FMD (Busse R, Fleming I, Hecker M. Signal transduction in endothelium-dependent vasodilation. *Eur Heart J.* 1993;14:Suppl I,2–9.; Busse R, Fleming I. Pulsatile stretch and shear stress: physical stimuli determining the production of endothelium-derived relaxing factors. *Journal of Vascular Research.* 1998;35:73–84.). Wall shear stress levels were compared to baseline vessel diameter (see FIG. 5). Systolic WSS during peak hyperemia (a measure of endothelial stimulus) is inversely determined by baseline diameter (r=0.47, p=0.049, see FIG. 5). Thus, small vessels experience greater WSS stimulus during peak hyperemia than large vessels. We also analyzed the relationship in the same vessels to the dilation response, and FDM response is greater in small vessels (r=0.62, p=0.006, see FIG. 5). The results of this study explain why flow mediated dilation, a measure of endothelial response to hyperemia, is greater in small arteries (see FIG. 5), because the WSS stimulus is greater in small arteries.

Table 2

Comparison of Diameter Measurements between Ultrasound and MRI

| Subject | Age | RF | D base U/S | D base MRI | D 1 U/S | D 1 MRI | )D U/S | )D MRI | %) D (mm) U/S | %) D (mm) MRI |
|---|---|---|---|---|---|---|---|---|---|---|
| 1 | 46 | M | C,F | | 3.21 | | 3.70 | | 0.49 | | 15.3 |
| 2 | 30 | F | | | 3.49 | | 4.19 | | 0.70 | | 20.1 |
| 3 | 56 | F | C,H | | 3.29 | | 3.58 | | 0.29 | | 8.8 |
| 4 | 31 | M | | | 5.09 | | 5.54 | | 0.45 | | 8.8 |
| 5 | 38 | M | | | 5.02 | | 5.61 | | 0.59 | | 11.8 |
| 6 | 39 | M | | | 4.85 | | 5.42 | | 0.57 | | 11.8 |
| 7 | 45 | F | | | 3.93 | | 4.27 | | 0.34 | | 8.7 |
| 8 | 41 | F | | | 3.69 | | 4.12 | | 0.43 | | 11.7 |
| 9 | 38 | M | | | 4.28 | | 4.94 | | 0.66 | | 15.4 |
| Mean | 40 | | | 4.09 | 3.88 | 4.60 | | 0.50 | | 12.4 |
| (St Dev) | | | 3.70 | † | (.60) | ‡ | 0.18 | * | 4.4 | * |

RF indicates cardiac risk factors; C, high cholesterol; H, hypertension; F, family history of coronary artery disease in a first degree relative; D base indicates baseline diameter; D 1 min, diameter at 1 minute after cuff release; U/S, measurement by ultrasound; MRI, diameter measurement by magnetic resonance imaging; * indicates a difference between the two modalities (p<0.0001); †, (p=0.001); ‡, (p=0.03).

Although a preferred embodiment of the invention has been described using specific terms, such description is for illustrative purposes only, and it is to be understood that changes and variations may be made without departing from the spirit or scope of the following claims.

What is claimed is:

1. A non-invasive method of assessing vascular endothelial function, comprising:
   (a) using a magnetic resonance imaging scanner to perform phase contrast magnetic resonance imaging to obtain images;
   (b) locating an artery of a subject using coronal scout images;
   (c) positioning the subject, whereby the artery is parallel to a magnet bore of the magnetic resonance imaging scanner;
   (d) acquiring a baseline image of the artery;
   (e) constricting the artery for a time period, whereby the artery is fully occluded;
   (f) releasing the artery from occlusion;
   (g) acquiring images of the artery during occlusion, and at time periods following release from occlusion;
   (h) calculating wall shear stress and flow mediated dilation of the artery from data obtained from said baseline image and said images acquired during occlusion and following occlusion;
   (i) determining a relationship between wall shear stress and flow mediated dilation; and
   (j) determining if the relationship between wall shear stress and flow mediated dilation lies in a normal range, whereby lying in a normal range is indicative of normal vascular endothelial function.

2. A non-invasive method of determining a relationship between shear stress stimulus during hyperemia and dilation response in a subject comprising:
   (a) using a magnetic resonance imaging scanner to perform phase contrast magnetic resonance imaging to obtain images;
   (b) locating an artery of a subject using coronal scout images;
   (c) positioning the subject, whereby the artery is parallel to a magnet bore of the magnetic resonance imaging scanner;
   (d) acquiring baseline images of the artery;
   (e) constricting the artery for a time period, whereby the artery is fully occluded; releasing the artery from occlusion;
   (g) acquiring images of the artery during occlusion, and at time periods following release of occlusion;
   (h) calculating wall shear stress and flow mediated dilation of the artery from data obtained from said baseline image and said images acquired during occlusion and following occlusion; and
   (i) determining a relationship between shear stress stimulus during hyperemia and dilation response.

3. A non-invasive method of determining arterial wall shear stress during hyperemic response in a subject comprising:
   (a) using a magnetic resonance imaging scanner to perform phase contrast magnetic resonance imaging to obtain images;
   (b) locating an artery of a subject using coronal scout images;
   (c) positioning the subject, whereby the artery is parallel to a magnet bore of the magnetic resonance imaging scanner;
   (d) acquiring a baseline image of the artery;
   (e) constricting the artery for a time period, whereby the artery is fully occluded;

(f) releasing the artery from occlusion;

(g) acquiring images of the artery during occlusion, and at time periods following release of occlusion; and (h) calculating wall shear stress of the artery at baseline, during occlusion, and following release of occlusion from data obtained from said baseline image and said images acquired during occlusion and following occlusion.

4. A non-invasive method of determining a relationship between arterial diameter and hyperemic wall shear stress in humans, comprising:

(a) using a magnetic resonance imaging scanner to perform phase contrast magnetic resonance imaging to obtain images;

(b) locating an artery of a subject for imaging using coronal scout images;

(c) positioning the subject, whereby the imaged artery is parallel to a magnet bore of the magnetic resonance imaging scanner;

(d) acquiring a baseline image of the imaged artery;

(e) calculating baseline diameter of the imaged artery using data from the image;

(f) constricting an artery for a time period, whereby the artery is fully occluded and wherein the occluded artery is either identical to the imaged artery or a related artery which initiates from or branches into the imaged-artery;

(g) releasing the occluded artery from occlusion;

(h) acquiring images of the constricted artery during occlusion, and at time periods following release of occlusion;

(i) calculating wall shear stress following release of occlusion from data obtained from said baseline image and said images acquired during occlusion and following occlusion; and (j) determining a relationship between the wall shear stress immediately following release of occlusion and the baseline diameter of the constricted artery.

5. The method of any one of claims 1–3, wherein the subject is a human patient.

6. The method of-any one of claims 1–4, wherein constriction of the artery is accomplished through use of one of a sphygmomanometer, a tourniquet, and any other means of constriction which is releaseable.

7. The method of any one of claims 1–4, wherein said baseline image and said images acquired during occlusion and following occlusion are magnitude images and phase images.

8. The method of any one of claims 1–4, wherein the time periods following release of occlusion are between immediately after occlusion release and fifteen minutes after occlusion release.

9. The method of any one of claims 1–4, wherein the time period for constricting the artery is between about 30 seconds and about 7 minutes.

10. The method of any one of claims 1–4, wherein the artery is one of artery of an arm, an artery of a leg, a pulmonary artery, and a coronary artery.

11. The method of claim 2, further including the step of determining a relationship between dilation response value and one of shear stress stimulus and a change in shear stress from baseline to peak hyperemia.

12. A method of screening patients for abnormal vascular endothelial functioning, comprising:

(a) using a magnetic resonance imaging scanner to perform phase contrast magnetic resonance imaging to obtain images;

(b) locating a brachial artery of a patient using coronal scout images;

(c) positioning the patient, whereby the artery is parallel to a magnet bore of the magnetic resonance imaging scanner;

(d) acquiring a baseline image of the artery;

(e) constricting the artery for a time period, whereby the artery is fully occluded;

(f) releasing the artery from occlusion;

(g) acquiring images of the artery during occlusion, and at time periods following release from occlusion;

(h) calculating wall shear stress and flow mediated dilation of the artery from data obtained from said baseline image and said images acquired during occlusion and following occlusion;

(i) determining a relationship between wall shear stress and flow mediated dilation; and (j) determining if the relationship between wall shear stress and flow mediated dilation does not lie in a normal range, whereby not lying in a normal range is indicative of abnormal vascular endothelial function.

13. The method of claim 12, further including the steps of determining a pattern of wall shear stress during occlusion and resulting hyperemia; and comparing said pattern to a normal pattern.

14. A method of calculating arterial wall shear stress using phase contrast magnetic resonance angiography comprising:

(a) performing phase contrast magnetic resonance scans of an artery before, during, and after hyperemia; and (b) using measurements of arterial cross sectional area (A), spatially averaged flow velocity (Vsa) across the arterial cross section, and central flow velocity (Vc) of the arterial cross section obtained from said phase contrast magnetic resonance angiography scans of the artery before, during, and after hyperemia and calculating wall shear stress.

15. The method of claim 14 wherein:

$n = 2/(Vc/Vsa) - 1$, $D = 2(A/\pi)^{1/2}$,

Wall shear rate = $2(n+2)(Vsa)/D$, and

Wall shear stress = Wall shear rate (viscosity), and these calculations are used in determination of wall shear stress from data resulting from phase contrast magnetic resonance angiography scans.

* * * * *

UNITED STATES PATENT AND TRADEMARK OFFICE
CERTIFICATE OF CORRECTION

PATENT NO.    : 6,654,628 B1
DATED         : November 25, 2003
INVENTOR(S)   : Harry A. Silber, Joao A.C. Lima and David A. Bluemke It is certified that error appears in the above-identified patent and that said Letters Patent is hereby corrected as shown below:

<u>Title page,</u>
Item [75], Inventors, please replace "Jaoa A.C. Lima" with -- Joao A.C. Lima --

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,654,628 B1 | Page 1 of 1 |
| APPLICATION NO. | : 09/706359 | |
| DATED | : November 25, 2003 | |
| INVENTOR(S) | : Silber et al. | |

It is certified that error appears in the above-identified patent and that said Letters Patent is hereby corrected as shown below:

Please replace the following paragraph: col. 1, line 4 as follows:

FEDERALLY SPONSORED RESEARCH OR DEVELOPMENT
This invention was made with Government support under HC095168 awarded by the National Institutes of Health. The Government has certain rights in the invention.

Signed and Sealed this
Third Day of January, 2012

David J. Kappos
*Director of the United States Patent and Trademark Office*